US005721367A

United States Patent [19]

Kay et al.

[11] Patent Number: 5,721,367

[45] Date of Patent: *Feb. 24, 1998

[54] HOMOLOGOUS RECOMBINATION IN MAMMALIAN CELLS

[75] Inventors: Robert M. Kay, San Francisco, Calif.; Anton Berns, Spaarndam, Netherlands; Paul Krimpenfort, Heemstede, Netherlands; Frank Pieper, Utrecht, Netherlands; Rein Strijker, Oegstgeest, Netherlands

[73] Assignee: Pharming B.V., Leiden, Netherlands

[ * ] Notice: The term of this patent shall not extend beyond the expiration date of Pat. No. 5,612,205.

[21] Appl. No.: 462,986

[22] Filed: Jun. 5, 1995

Related U.S. Application Data

[63] Continuation of Ser. No. 989,002, Mar. 1, 1993, Pat. No. 5,612,205, and a continuation-in-part of Ser. No. 574,747, Aug. 29, 1990, abandoned.

[51] Int. Cl.[6] .............................. C12N 15/00; C12N 5/00; C12P 21/06; C12P 21/04

[52] U.S. Cl. .......................... 800/2; 435/172.3; 435/240.1; 435/69.1; 435/69.7

[58] Field of Search .............................. 800/2; 435/172.3

[56] References Cited

FOREIGN PATENT DOCUMENTS 4701589 6/1990 Australia .
9005188 5/1990 WIPO .

OTHER PUBLICATIONS

Sangos et al. Adv in Genetics 24: 285, 1987.

Lorenz et al. NAR 15(23): 9667, 1987.

Palmier et al in Genetic Manipulation, 1985, CSH pp. 123–132.

Van Zijl et al J. of Virology 62(6): 2191, 1988 Staueil et al.

*Primary Examiner*—Suzanne E. Ziska
*Attorney, Agent, or Firm*—Townsend & Townsend & Crew

[57] ABSTRACT

The invention relates to methods for intracellularly producing DNA segments by homologous recombination of smaller overlapping DNA fragments and transgenic mammalian cells and transgenic non-human mammals produced by such methods.

23 Claims, 11 Drawing Sheets

HOMOLOGOUS RECOMBINATION IN MAMMALIAN CELLS

This is a Continuation of application Ser. No. 07/989,002 filed Mar. 1, 1993, now U.S. Pat. No. 5,612,205 and is a continuation-in-part of U.S. Patent application Ser. No. 07/574,747 filed Aug. 29, 190, now abandoned.

TECHNICAL FIELD OF THE INVENTION

The invention relates to methods for making transgenic mammalian cells and transgenic non-human mammals by intracellularly producing DNA segments by homologous recombination of smaller DNA fragments; as well as transgenic mammalian cells and transgenic non-human mammals produced by such methods.

BACKGROUND OF THE INVENTION

A transgenic cell or animal contains one or more transgenes within its genome. A transgene is a DNA sequence integrated at a locus of a genome, wherein the transgenic DNA sequence is not otherwise normally found at that locus in that genome. Transgenes may be made up of heterologous DNA sequences (sequences normally found in the genome of other species) or homologous DNA sequences (sequences derived from the genome of the same species). Transgenic animals have been reported. For example, U.S. Pat. No. 4,736,866 discloses a transgenic mouse containing a c-myc oncogene. Other reports of transgenic animals include PTC Publication No. WO82/04443 (rabbit β-globin gene DNA fragment injected into the pronucleus of a mouse zygote); EPO Publication No. 0 264 166 (Hepatitis B surface antigen and Tissue Plasminogen Activator genes under control of the whey acid protein promoter for mammary tissue specific expression); EPO Publication No. 0 247 494 (transgenic mice containing heterologous DNA encoding various forms of insulin); PTC Publication No. WO88/00239 (tissue specific expression of DNA encoding factor IX under control of a whey protein promoter); PTC Publication No. WO88/01648 (transgenic mammal having mammary secretory cells incorporating a recombinant expression system comprising a mammary lactogen-inducible regulatory region and a structural region encoding a heterologous protein); and EPO Publication No. 0 279 582 (tissue specific expression of chloramphenicol acetyltransferase under control of rat β-casein promoter in transgenic mice).

Transgenic plants have also been produced. For example, U.S. Pat. No. 4,801,540 to Hiatt, et al., discloses the transformation of plant cells with a plant expression vector containing DNA encoding tomato polygalacturonase (PG) oriented in the opposite orientation for expression. The anti-sense RNA expressed from this gene is reportedly capable of hybridizing with the endogenous PG mRNA to suppress translation.

The transgenes introduced into animals and plants so far have been of relatively short length (generally less than about 50 kb). Many eukaryotic genes, however, cover large regions of genomic DNA with many and often very large intervening sequences (introns) between those sequence portions (exons) encoding mRNA. Further, many eukaryotic genes are bounded by regulatory sequences, e.g. enhancers, tissue-specific regulators, cis-acting elements and other physically linked regulatory elements sometimes located many thousands of nucleotides away from the structural gene. The manipulation of such eukaryotic genes has been impeded by their size and complexity. Obstacles include difficulty in the construction, stability, packaging and physical manipulation of large DNA molecules.

Vehicles for cloning DNA have inherent limitations on the size of the DNA they are able to accommodate. Traditional viral vectors such as lambda phage and SV40 have limits of packaging foreign DNA of approximately 50 and 5 kb, respectively. More recently the use of F and P1-based cloning systems, and the cloning of yeast artificial chromosomes have made it possible to propagate larger, contiguous pieces of DNA.

A yeast artificial chromosome or YAC vector, is generated by ligating sequences from a yeast chromosome onto the ends of a piece of DNA. Such sequences include a centromere, two telomeres (one on each end), an origin of replication, and a selectable marker. A telomere is located on each end of the particular piece of DNA to be cloned with a centromere interposed between one of the telomeres and the DNA to be cloned. Several groups have reportedly constructed yeast libraries containing 50–200 kb of human DNA in such YAC vectors (Burke, et al. (1987), *Science,* 236, 806–812; Traver, et al. (1989), *Proc. Natl. Acad. Sci. USA,* 86, 5898–5902). Recently, yeast libraries using polyamine condensation to reduce size bias during the yeast transformation step have been reported (McCormick, et al. (1989), *Proc. Natl. Acad. Sci. USA,* 86, 9991–9995). Libraries produced by this method have an average insert size of 410 kb. Unfortunately, yeast chromosomes are quite difficult and more time consuming to prepare in bulk than are plasmids or viral vectors. Furthermore, there is only one copy of the YAC vector per yeast cell, necessitating the growth of large quantities of the yeast clone for transformations or transfections. Finally, yeast colonies are more laborious to screen than are bacterial colonies and it is not currently possible to ligate such large YAC derived linear DNA segments into circular DNA to transform them into bacteria.

Another method of propagating relatively large DNA molecules involves the use of the P1 cloning system. Sternberg, N. (1990) *Proc. Natl. Acad. Sci. USA,* 87, 103–107. Vector plasmids for this system contain a P1 packaging site (pac) which is required to initiate the packing of the vector plasmid into the P1 bacteriophage head. The vector plasmid also contains two P1 loxP recombination sites flanking the cloned insert, which are necessary to circularize the packaged linear DNA after P1 phage infection of cells containing the P1 Cre recombinase. The maximum insert size of this system is reported to be about 100 kb because the P1 phage head can accommodate only between 110 and 115 kb of DNA.

Another recently developed method of generating and propagating large pieces of DNA involves the use of F factor-based plasmids. This method reportedly uses sequential homologous recombination steps in *E. coli* between two closed circular plasmids to sequentially build larger plasmids. Each round of recombination increases the size of the DNA insert in the plasmid. Several plasmids containing 150 kb inserts using this technique have been reported (O'Conner, et al. (1989), *Science,* 744, 1307–1312). A disadvantage of this approach is that the multi-step procedure is laborious, and requires careful analysis to ensure that rearrangement artifacts have not been introduced. Additionally, even though the technique provides for the production of supercoiled plasmids containing the construct of interest, the large DNA inserts contained therein nevertheless are subject to mechanical shearing when excised. Excision of such inserts is reportedly necessary since plasmid sequences have a negative influence on expression of the transgene (Brinster, et al. (1985), *Proc. Natl. Acad. Sci. USA,* 82, 4438–4442).

Despite these techniques for propagating larger pieces of DNA, relatively small DNA inserts (e.g. 40–50 kb) continue to be used to transform cultured mammalian cells and to generate transgenic animals.

The invention overcomes the foregoing and other limitations (including the diffiuclty in constructing large DNA molecules) by using homologous recombination in an exquisitely simple way. Although extensive research has been conducted on homologous recombination, the solution to the aforementioned problems in mammalian cell transformation is not apparent from such research.

Gene targeting refers to the directed modification of a selected chromosomal locus of an endogenous chromosome of a cell by homologous recombination with an exogenous DNA sequence having homology to the selected endogenous sequence. Gene targeting has been employed to enhance, modify and disrupt expression of endogenous genes. (See Bollag, et al. (1989), *Ann. Rev. Genet.*, 23, 199–225). A significant obstacle to efficient gene targeting in mammalian cells is the ability of these cells to nonhomologously integrate transfected DNA (see Roth and Wilson (1988) In Genetic Recombination, ed. Kucherlapati and Smith, pp. 621–653, Washington, D.C.: Am. Soc. Microbiol.; Brinster, et al. (1985), *Proc. Natl. Acad. Sci. USA* 82, 4438–4442). Recently, positive-negative selection vectors have been described for selecting those cells wherein the vector has integrated into a genome by homologous recombination (see e.g. Mansour, S. L., et al. (1988), *Nature*, 336, 348–352 and Capecchi (1989), *Science*, 244, 1288–1292).

Extrachromosomal homologous recombination refers to homologous recombination occurring within a cell between two exogenous, transfected, and at least partially homologous DNA sequences. This phenomena has reportedly been demonstrated by performing extrachromosomal gene or virus "rescue" experiments (van Zijl et. al (1988), J. Virol., 62, 2191–2195; Miller and Temin (1983), *Science*, 220, 606–609; Wong and Capecchi (1987), *Mol. Cell. Biol.*, 7, 2294–2295; and for recent review see, Bollag, et al. (1989), *Ann. Rev. Genet.*, 23, 199–225). In these studies overlapping pieces of DNA, typically constituting in composite a functional virus, were introduced into cultured cells. Within the cell, the virus sub-fragments were reported to homologously recombine to reconstitute viable virus particles. For instance, van Zijl et. al, transfected, using calcium phosphate precipitation, five overlapping cloned subgenomic fragments of the pseudorabies virus into cultured cells. Some fragments reportedly recombined to form viable virus. Such studies have been directed primarily at manipulating viral genomes, elucidating the mechanisms of and variables affecting efficiency and accuracy of homologous recombination.

Other examples of extrachromosomal homologous recombination involve the introduction of plasmids containing DNA encoding two related but distinct polypeptides in bacterial cell culture. Recombination between the genes encoding such parental polypeptides results in hybrid genes encoding hybrid polypeptides. See e.g. Schneider, W. P. et al. (1981), *Proc. Natl. Acad. Sci. USA*, 78, 2169–2173 (tryp A); Weber and Weissmann (1983) *Nucl. Acids Res.*, 11, 5661–5669 (alpha interferons); Gray, G. L. et al. (1986), *J. Bacteriol.*, 166, 635–643 (alpha amylases); and EPO Publication No. 0 208 491 published Jan. 14, 1987.

One laboratory has reported extrachromosomal gene rescue in the mouse zygote (Palmiter, et al. (1985) in: Genetic Manipulation of the Early Mammalian Embryo, Cold Spring Harbor Laboratory, p. 123–132). Previously, these investigators reported fusing the mouse metallothionein-I (MT) promoter to the gene for human growth hormone (hGH) (Palmiter, et al. (1983), *Science*, 222, 809–814) to produce transgenic mice that expressed the MT-hGH transgene and grew larger than control mice. Subsequently, these investigators reported the construction of two deletion mutants of the MT-hGH DNA transgene (Palmiter, et al. (1985), supra). In one mutant a 5' portion of the MT-hGH DNA segment was deleted. In a second mutant, a portion within the 3' half of the MT-hGH DNA segment was deleted. These investigators reportedly performed a control to a gene rescue experiment by co-injecting the deletion mutants into normal fertilized mouse eggs. Some of the resultant mouse pups reportedly expressed mRNA corresponding to the intact MT-HGH gene and grew larger than their littermates. The mechanism of this rescue remains unclear.

The references discussed above are provided solely for their disclosure prior to the filing date of the present application. Nothing herein is to be construed as an admission that the inventors are not entitled to antedate such disclosure by virtue of prior invention or priority based upon one or more previously filed applications.

SUMMARY OF THE INVENTION

It is an object herein to provide methods for making transgenic mammalian cells and transgenic mammals. It is also an object herein to provide that the aforementioned methods are capable of generating transgenes longer than 50 kb. Further, it is an object herein to provide transgenic mammalian cells and transgenic mammals produced by the aforementioned methods.

In accordance with the foregoing objects, the invention includes methods for making transgenic cells by introducing into a mammalian cell at least two DNA fragments. The DNA fragments have 5' and 3' sequence portions, wherein the first fragment 3' sequence portion is substantially homologous to the second fragment 5' sequence portion. Inside the cell, these DNA fragments homologously recombine to form a recombined DNA segment at least 50 kb long which integrates into the cell's genome.

In addition, the invention includes methods for making transgenic cells by introducing into a mammalian cell at least first, second and third fragments. Each of the DNA fragments have 5' and 3' sequence portions, wherein the first fragment 3' sequence portion is substantially homologous to the second fragment 5' sequence portion. Further, the second fragment 3' sequence portion is substantially homologous to the third fragment 5' sequence portion. Inside the cell, these DNA fragments homologously recombine to form a recombined DNA segment which integrates into the cells's genome.

The invention also includes methods for making transgenic cells by introducing into a mammalian cell multiple copies of a DNA molecule generally greater than 50 kb in length which integrates into the genome of said cell.

The invention also includes methods for making transgenic mammals. These embodiments proceed as described for transgenic mammalian cells except that the DNA fragments or molecules are introduced into a mammalian zygote or pluripotent stem cell such as an ES cell. The zygote or pluripotent stem cell is then used to generate a transgenic mammal by conventional methods.

Still further, the invention includes transgenic mammalian cells and transgenic mammals containing transgenes made according to the aforementioned methods of the invention.

DETAILED DESCRIPTION OF THE PREFERRED EMBODIMENTS

The inventors have discovered that when two or more overlapping DNA fragments are introduced into a recombination competent cell such as a mammalian zygote that such DNA fragments homologously recombine and integrate into the genome of the recipient cell. This discovery has far reaching consequences not only in the transgenic field but also in the manipulation of exogenous DNA within mammalian cells in general.

As used herein, the term "DNA fragment" refers to a fractional piece of a DNA segment which is to be incorporated into the genome of a mammalian cell as a transgene. Each DNA fragment has at least one sequence portion that is substantially homologous to a sequence portion of another DNA fragment such that when two or more DNA fragments are co-introduced into a recombination competent mammalian cell, they homologously recombine at their region of homology. Preferably the sequence homology is at or near the ends of the DNA fragments. Further, each fragment contains a DNA sequence portion which is not homologous to the sequence in the other DNA fragment(s) with which it recombines.

As used herein, a recombined "DNA segment" refers to DNA formed by the intracellular homologous recombination of two or more DNA fragments. Such recombination of fragments results in a DNA segment having a length greater than that of any of the DNA fragments used to form it by in vivo homologous recombination. Since the DNA fragments used to form a recombined DNA segment are distinct DNA fragments having regions of sequence homology and regions of non-homology, the recombined DNA segments so formed are distinguishable from the multicopy head-to-tail complexes formed in mammalian cells when multiple copies of DNA are introduced therein. Folger, K. R., et al. (1982), *Mol. Cell. Biol.*, 2, 1372–1387.

Figure 1:
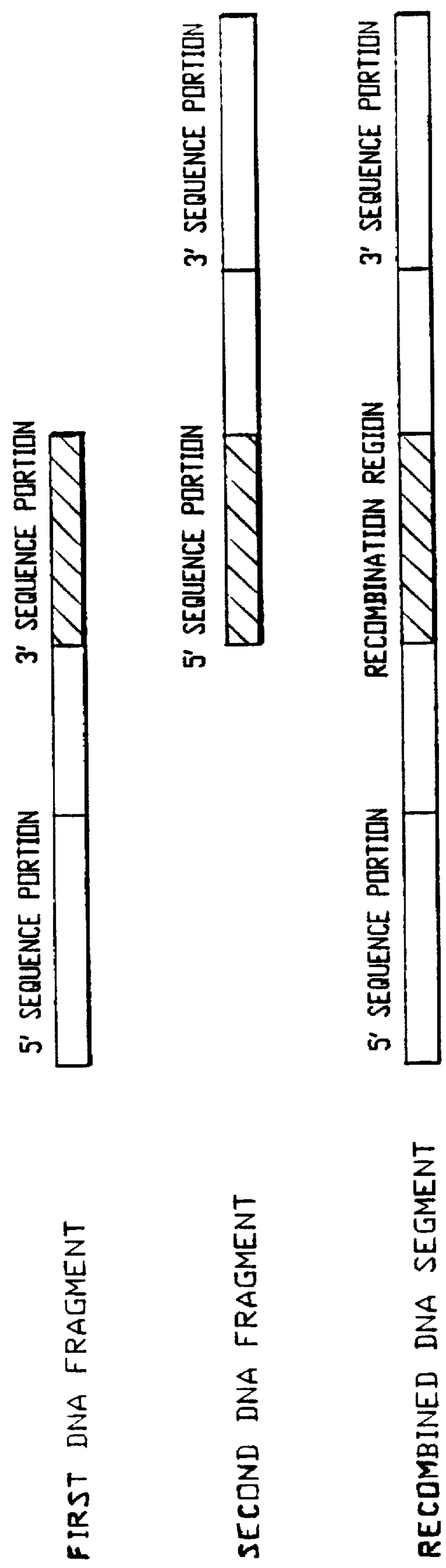
FIG. 1 depicts the generation of a DNA segment by homologous recombination of two DNA fragments.

A DNA segment formed from the recombination of two DNA fragments is depicted in FIG. 1. This diagram shows first and second DNA fragments, together with the DNA segment which is formed by the recombination of the first and second fragments. As can be seen, the first and second DNA fragments each have a 5' and a 3' sequence portion. After homologous recombination of the DNA fragments, the first DNA fragment 5' sequence portion becomes the 5'-most sequence portion of the recombined DNA segment. Similarly, the second DNA fragment 3' sequence portion becomes the 3'-most sequence portion. The first DNA fragment 3' sequence portion and the second fragment 5' sequence portion are substantially homologous and correspond to the recombination region of the DNA segment shown in FIG. 1. The remainder of the DNA sequence in each of these fragments is non-homologous as between the DNA fragments. The choice of DNA fragments will be apparent based on the disclosure and examples herein.

Figure 2:
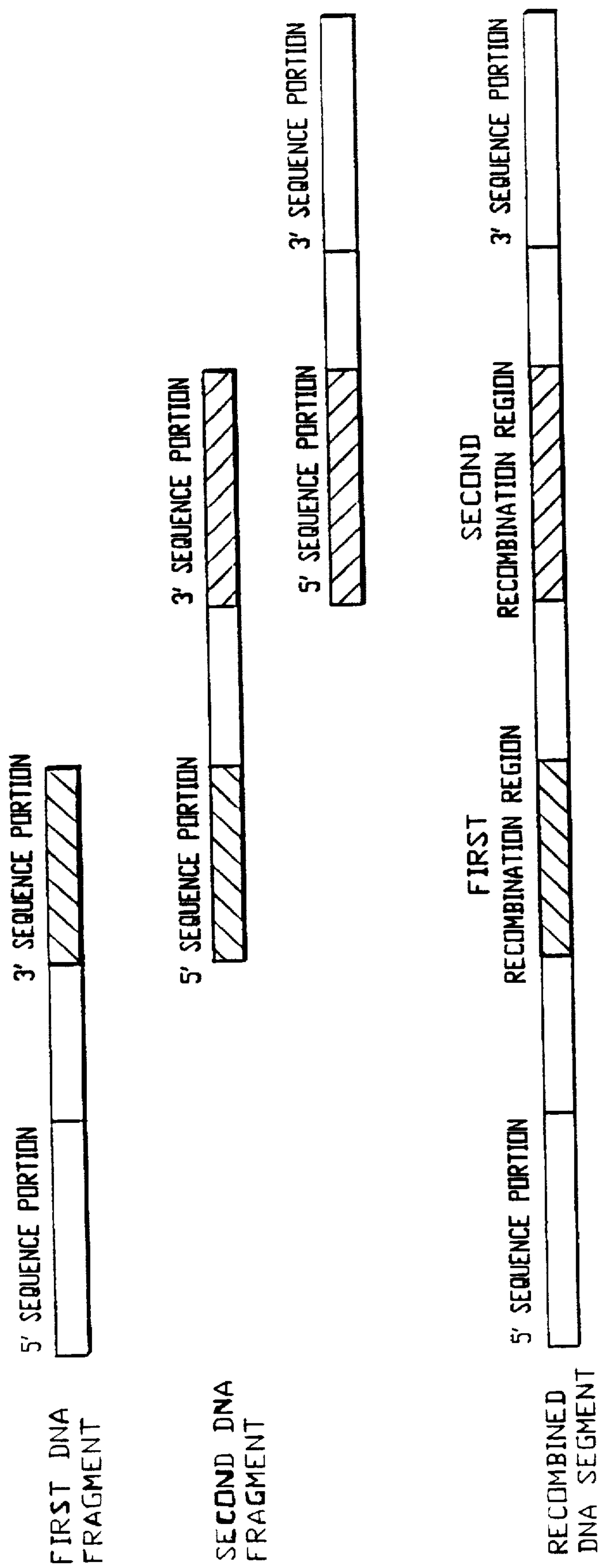
FIG. 2 depicts the generation of a DNA segment by homologous recombination of three DNA fragments.

A DNA segment formed from the recombination of three DNA fragments is depicted in FIG. 2. As can be seen, the first sequence portion and first recombination region correspond to the recombined segment of FIG. 1. The second DNA fragment 3' sequence portion and the third fragment 5' sequence portion are substantially homologous and correspond to the second recombination region of the DNA segment shown in FIG. 2. Here, the third DNA fragment 3' sequence portion becomes the 3'-most sequence portion of the recombined DNA segment. Although only three DNA fragments are depicted in FIG. 2, more than three DNA fragments may be used to practice the invention.

In the preferred embodiments double stranded DNA is used. When such is the case, the terminology 5' and/or 3' refers to the orientation of the above-described sequences relative to one of the strands of the recombined DNA segment formed by homologous recombination of DNA fragments. Although the choice of strand is arbitrary, when used to describe a DNA segment encoding an expressible gene, the description of the DNA segment will be read 5' to 3' on the sense strand.

Figure 3:
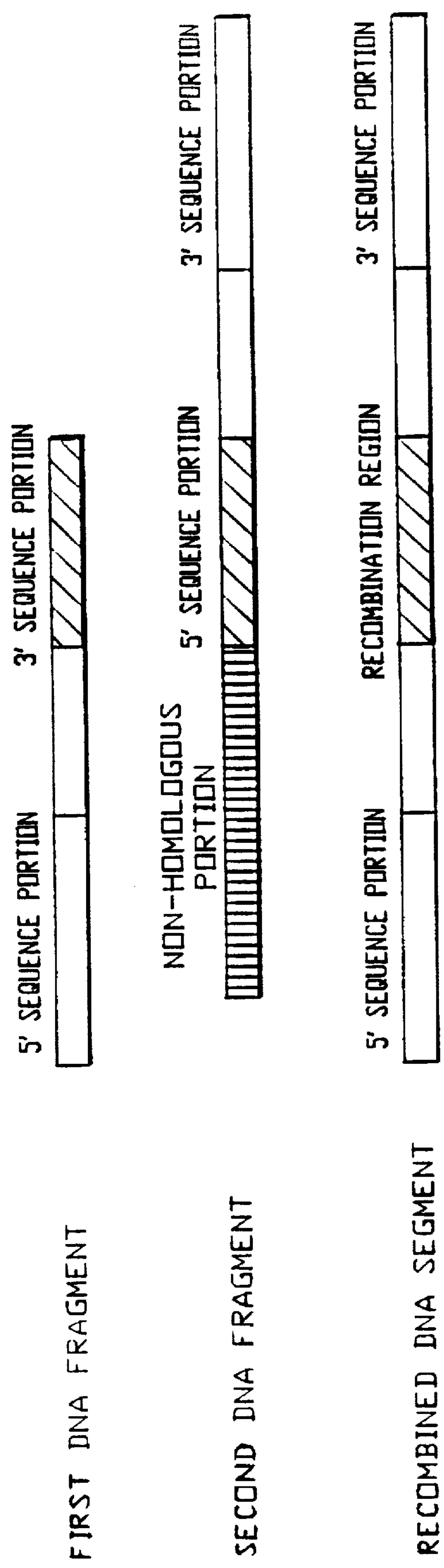
FIG. 3 depicts the generation of a DNA segment by homologous recombination of two DNA fragments one of which incorporates an additional flanking region distal to the 5' region of homology.

Although the foregoing description describes the various homologous sequence portions as being located at the ends of the various DNA fragments, it is to be understood that these sequence portions need not be so located. For example, FIG. 3 is similar to FIG. 1 wherein two DNA fragments homologously recombine to form a recombined DNA segment. However, in FIG. 3, the 5' sequence portion of the second DNA fragment (which is substantially homologous to the 3' sequence portion of the first DNA fragment) is not located at the 5' terminus of the second DNA fragment. While the 5' sequence portion is oriented on the DNA fragment 5' relative to the 3' sequence portion, there exists another, non-homologous sequence situated 5' to the 5' sequence portion. During homologous recombination such 5' (or 3') terminal regions which are not homologous are excised and are consequently excluded from the resultant DNA segment (see FIG. 3).

The invention can be practiced in any "recombination competent mammalian cell". Such cells may be defined functionally as those which are capable of homologously recombining DNA fragments which contain regions of substantial overlapping homology. Such cells contain endogenous recombinases, or are genetically engineered to contain such recombinases, and such other necessary components that are required to mediate DNA recombination. Examples of recombination competent mammalian cells include endothelial cells, epithelial cells, myoblasts, hepatocytes, leukocytes, hematopoietic stem cells, fibroblasts, common cultured cells such as HeLa cells and Chinese hamster ovary cells (CHO), and embryonic target cells.

As used herein, an "embryonic target cell" is defined as any cell that is capable of populating the germ line of a mammal with the genome of the embryonic target cell and transmitting genomic material originally from the embryonic target cell to progeny of such a mammal.

Examples of embryonic target cells include zygotes such as those from bovine, murine, ovine, porcine and non-human primate species as well as rat, rabbit and guinea pig. Particularly preferred zygotes are those of murine, bovine and porcine species, preferably murine and bovine species and most preferably murine species.

Other embryonic target cells useful in practicing the invention include embryonic stem cells (ES cells). ES cells are obtained from pre-implantation embryos cultured in vitro. (Evans, N. J. et al. (1981), *Nature* 292, 154–156; Bradley, M. O. et al. (1984), *Nature*, 309, 255–258; Gossler, et al. (1986), *Proc. Natl. Acad. Sci. USA*, 83, 9065–9069; and Robertson, et al. (1986), *Nature*, 322, 445–448. Such ES cells may be derived from any number of species including bovine, murine, ovine, porcine and non-human primate species as well as rat, rabbit and guinea pig. ES cells preferably are of mouse or rat origin, most preferably of mouse origin.

The method of introduction of DNA fragments into recombination competent mammalian cells can be by any method which favors co-transformation of multiple DNA molecules. The method of introduction of DNA fragments into a zygote or ES cell is preferably micro-injection into a pronucleus in the case of the zygote (fertilized oocyte) or the nucleus in the case of the ES cell. Alternatively, the DNA segment of the invention may be formed in ES cells by introducing the appropriate DNA fragments by calcium phosphate mediated transformation. Dextran sulfate mediated transformation and other methods known to those skilled in the art, such as electroporation, may also be used.

Preferred methods for introducing the DNA fragments of the invention into other recombination competent mammalian cells include microinjection and electroporation, most preferably microinjection. In addition, the aforementioned methods for transforming ES cells may also be used.

Generally, when the zygote is targeted for transgenesis, the first generation transgenic mammal derived according to the methods herein will be heterozygous or chimeric for the transgene. Accordingly, the transgene will generally be found in all somatic cells of the transgenic mammal as well as half of the gametes it produces. Therefore, the invention also provides for the breeding of two such heterozygous transgenic animals to form offspring that are homozygous for the transgene; i.e. there are two copies of the transgene per diploid animal cell—one incorporated within a maternal chromosome and the other within the corresponding paternally derived chromosome. In this case, the transgene will generally be found in all nucleated cells of the animal, including all the gametes produced, and so will always be passed on to subsequent offspring. It is also possible that the first animal produced from the zygote is a chimeric animal (i.e. only some of it's cells contain the transgene). This might occur, for example, if a cell of the early embryo loses it's transgene or if the genome of the micro-injected zygote replicates before the transgene integrates. So long as progeny of transgenic cells are represented in the germ line, it is possible to obtain transgenic animals from the offspring of such chimeric animals.

In the case of the ES cell, the animal obtained after implantation and gestation is generally a chimetic (mosaic) animal wherein a subpopulation of the cells from such an animal contain the DNA segment (transgene). Such animals may be cross bred by methods well known to those skilled in the art to form fully transgenic animals containing the DNA segment in each of the somatic and germline cells of the animal.

Recombined DNA segments are not limited to any particular DNA sequence. The encoded sequence may be of purely synthetic origin (custom-made synthetic nucleic acids are routinely available with automated DNA synthesizers or may be purchased commercially) or may be derived from reverse transcription of mRNA sequences or derived directly from genomic DNA sequences. The DNA used to make transgenic cells and animals preferably comprises genomic DNA rather than cDNA. This is because the expression of transgenes is preferably limited to tissue-specific expression as well as temporal-specific expression. When the transgene is derived from genomic DNA, important cis-acting regulatory sequences such as enhancers and other regulatory elements, located either in introns or in regions distant from the structural gene can be included. Such regulatory sequences are lost during transcription and RNA processing and accordingly are not generally available with cDNA-derived transgenes.

Sequences derived from genomic DNA will generally encode at least a portion of a gene but may alternatively encode regions of untranscribed DNA or regions of unrecombined genetic loci. Examples of the latter include the immunoglobulin and T-cell antigen receptor loci. Generally however, the DNA segment includes a sequence which encodes an RNA transcript; preferably an mRNA transcript encoding a polypeptide. Examples of important polypeptides include milk proteins such as lactoferrin, lysozyme, lactalbumin, bile salt-stimulated lipase, secreted immunoglobulins, etc.; serum proteins such as albumin, immunoglobulins, Factor VIII, Factor IX, tissue plasminogen activator, etc.; and other proteins such as dystrophin, cystic fibrosis associated protein and industrially important enzymes. Examples of industrially important enzymes include bacterial and fungal proteases, lipases, chitinases and liginases.

The DNA molecules and segments of the invention may also be used for gene therapy. For example, an individual of a species may have one or more defective genes which produce an adverse phenotype. In such cases, selected populations of cells, e.g. bone marrow stem cells, lung stem cells, etc. can be extracted from the individual and then modified by the methods and compositions described herein to introduce the normal wild type gene into such stem cells (either by random integration or gene targeting) to correct or mitigate the pathology associated with the adverse phenotype. The so-modified cells are then reintroduced into the individual to generate lineages of mature cell types which carry the desired gene. Examples of such gene therapy include the generation of a gene segment encoding the normal cystic fibrosis gene, the normal hemoglobin gene, and the like.

When the polypeptide encoding transgene also contains appropriate regulatory sequences, it effects the expression of the polypeptide. In general, the cis-acting regulatory sequences controlling expression are chosen such that tissue-specific and/or temporal-specific expression is obtained. Further, to the extent secretion of such a polypeptide is desired, appropriate DNA sequences encoding secretory signal sequences functional in the particular cell type in which tissue specific expression occurs may also be incorporated into the DNA segment formed according to the invention. The choice of the DNA sequence for the recombined DNA segment will be readily apparent to those skilled in the art depending upon the particular polypeptide or particular application.

In one embodiment of the invention, the DNA fragments are "overlapping" portions of a gene. However, the invention also includes non-overlapping DNA fragments wherein the region of homology is a nucleotide sequence that has been ligated onto at least one end of at least one of the fragments. In a preferred embodiment, at least two different DNA fragments have substantially homologous synthetic DNA sequences ligated to their 5' and 3' ends, respectively.

The number of DNA fragments and the number of recombination events required to build the DNA segment depends on the length of the regions of homology, the length of the DNA fragments, and the length of the recombined DNA segment. The length of the regions of homology is partly dependent on the degree of the homology. As used herein "substantial homology" between two DNA sequence portions means that the sequence portions are sufficiently homologous to facilitate detectable recombination when DNA fragments are co-introduced into a recombination competent cell. Two sequence portions are substantially homologous if their nucleotide sequences are at least 40%, preferably at least 60%, more preferably at least 80% and most preferably, 100% identical with one another. This is because a decrease in the amount of homology results in a corresponding decrease in the frequency of successful homologous recombination. A practical lower limit to sequence homology can be defined functionally as that amount of homology which if further reduced does not mediate detectable homologous recombination of the DNA fragments in a recombination competent mammalian cell.

If non-homology does exist between the homologous sequence portions, it is preferred that the non-homology not be spread throughout the homologous sequence portion but rather in discrete areas of the homologous sequence portion. In any event, the lesser the degree of homology, the longer the region of homology should be in order to facilitate homologous recombination. Although as few as 14 bp of 100% homology are sufficient for homologous recombination in mammalian cells (Rubnitz, J. and Subramani, S. (1984), *Mol. Cell. Biol.*, 4, 2253–2258), longer homologous sequence portions are preferred, e.g. 500 bp, more preferably, 1000 bp, next most preferably about 1800 bp, and most preferably, greater than 1800 bp for each homologous sequence portion.

The frequency of correct transgenesis (correct recombination and integration of the complete DNA segment) depends on a number of factors including the number of DNA fragments, the size and degree of homology of the various regions of overlap, and properties inherent in the recombined DNA segment and the host genome. In some embodiments, the frequency of correct transgenesis is high enough that no selection is required. For example, in the case of the zygote, the frequency of homologous recombination and integration is sufficiently high that the number of zygotes microinjected is not impractical even without a means to select for recombination, i.e. the transgene need not encode a positive selection marker which confers a selectable phenotype upon homologous recombination. However, DNA encoding a gene which confers a selectable phenotype upon transformation, e.g. neomycin resistance, may be used by incorporating such a selectable gene in one of the DNA fragments.

Preferably, the number of zygotes to be microinjected to obtain a transgenic animal is less than one thousand; more preferably, less than 200. The percentage of microinjected zygotes that develop into animals is preferably at least one percent, more preferably at least five percent; most preferably at least twenty-five percent. Of the animals born, preferably at least one percent is transgenic; more preferably at least ten percent. Of the transgenic animals born, preferably at least ten percent contain a copy of a complete recombined DNA segment; more preferably, at least fifty percent.

In the embodiments of the invention, the DNA fragments are of any practical length. The minimum size is constrained only by the requirement that there be a region of homology long enough to facilitate homologous recombination. DNA fragments preferably each have a length of about 50 kb, more preferably about 100 kb. DNA fragments, however, can be longer than 100kb. Even if the length of the fragments is such that substantial sub-fragmentation occurs during manipulation of such fragments, such fragments can nevertheless be used to form a DNA segment by homologous recombination. This is because such sub-fragments are capable of recombining with each other to reconstitute the fragment. This occurs when multiple copies of the fragment are used and the fragmentation pattern is random such that the sub-fragments have overlapping regions of homology. In such circumstances, the DNA fragments can be considered to be identical "DNA molecules" as discussed infra.

DNA segments may be as small as a few hundred base pair cDNA clone or as large as a multi-mega base gene locus including regulatory regions necessary to obtain tissue-specific and temporal expression. Preferably, the recombined DNA segment has a length between 3.5 and 1000 kb, preferably between 50 and 500 kb; more preferably between 100 and 500 kb; and most preferably between 200 and 500 kb. Such recombined DNA segments, however, may be greater than 1000 kb.

In yet another embodiment of the invention, at least two identical "DNA molecules", generally at least about 50 kb in length, preferably at least 75 kb in length, more preferably at least 100 kb in length, and most preferably at least 200 kb in length are introduced directly into a recombination competent mammalian cell. While mechanical shearing may fragment such large DNA molecules, the resulting fragments are of random size. Further, since multiple copies of the molecule are introduced simultaneously, mechanical shearing or other processes produce a pool of overlapping fragments. Within the cell, overlapping fragments then recombine at their regions of homology. When a sufficient number of DNA molecules are introduced, e.g. by microinjection, the number of resultant overlapping fragments are such that at least one complete recombined DNA molecule is formed within the cell by homologous recombination of at least two fragments.

When introduced by microinjection, the number of copies of the DNA molecule will depend in part on the size of the DNA molecule. Since the volume of solution microinjected is limited by the size of the cell and the density of the solution is limited by viscosity constraints of the microinjection technique, in general, the longer the DNA molecule, the fewer number of copies are microinjected. Generally, between 2 and 1,000 DNA molecules are microinjected, preferably between 10 and 200, most preferably between 25 and 200.

Methods for cloning such large DNA molecules, including YAC vectors, P1-based vectors and F-based plasmids have been reported and discussed above. Fragmentation of the microinjected molecules can be ascertained by exposing a parallel test sample to the identical shearing forces. Fragmentation of the test sample is then separately determined by electrophoretic techniques, electron microscopy, gradient centrifugation, or other techniques known to those skilled in the art.

In addition to forming DNA segments that may be randomly integrated into the genome of a transgenic animal, the invention also includes the generation of DNA segments corresponding to positive-negative selection vectors which may be used to select ES cells wherein the vector is targeted to integrate into the genome at a specific site. Mansour, S. L., er al (1988), *Nature,* 336, 348–352, and Capecchi, M. (1989), *Science,* 244, 1288–1292.

Figure 4:
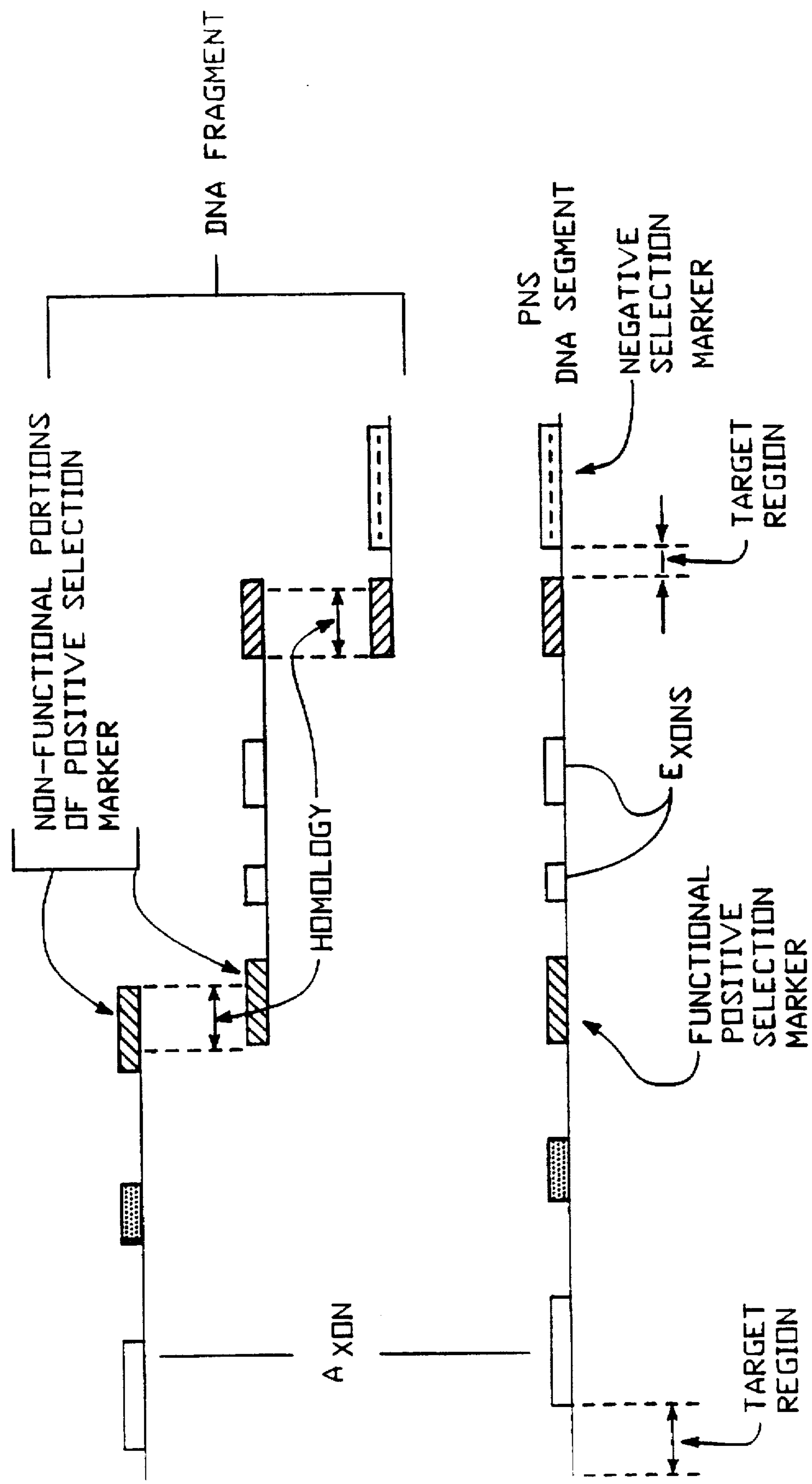
FIG. 4 depicts the construction of a positive-negative selection vector by way of homologous recombination of three DNA fragments.

The construction of the DNA segment corresponding to a positive-negative selection vector is depicted in FIG. 4. As indicated therein, a negative selection marker is situated at the 3' end of the PNS vector (referred to as a "PNS segment"). Located within an intron of the PNS vector is a positive selection marker. Also shown in the PNS vector of FIG. 4 are two target regions, each of which is homologous to a target DNA sequence within the genome of the ES cell to be injected. When nonhomologous random integration of the PNS vector occurs, the negative selection marker is incorporated. Cells containing such a PNS vector are thereafter selected against. When the PNS vector integrates into the genome by way of homologous recombination through the target regions, the negative selection marker is excised and not included in the genome. Cells wherein such homologous recombination has occurred may be selected based on the positive selection marker contained within the intron.

The DNA fragments which are used to construct such a PNS vector according to the present invention are also depicted in FIG. 4. As indicated, three DNA fragments containing overlapping regions are used to construct the PNS vector by simultaneous microinjection into the nucleus of an ES cell. The corresponding overlapping regions between the different DNA fragments are shown and correspond to the recombination regions depicted in the PNS vector. The ES cells wherein the DNA segment has integrated by homologous recombination are selected and thereafter implanted into a recipient female to yield a chimeric animal containing the DNA segment as a transgene.

In the following examples, a recombined DNA segment encoding human serum albumin was formed in mouse zygotes by co-injecting appropriate DNA fragments. The resultant transgenic mice obtained therefrom exhibited tissue-specific expression of the human serum albumin-containing gene segment in the mouse liver. As further indicated in Examples 2 and 3, DNA fragments encoding an unrearranged human immunoglobulin gene homologously recombine when microinjected into the pronucleus of a mouse zygote. In Example 2, two YAC derived fragments are microinjected and homologously recombine to form a larger recombined DNA segment. In Example 3, multiple copies of a large uncondensed YAC DNA molecule are microinjected. The processes associated with microinjection may subject these large DNA molecules to mechanical shearing forces. The resultant fragments, however, if formed, can homologously recombine to regenerate, intracellularly, a recombined DNA segment corresponding in sequence to the microinjected DNA molecules. Other examples are also set forth.

Although the specific examples disclose best modes for practicing the invention, it will be apparent to those skilled in the art that various modifications may be made to the disclosure herein and that such modifications are within the scope of the invention.

EXAMPLE 1

Transgenic Mice Containing the Human Serum Albumin (hSA) Transgene Generated by in vivo Homologous Recombination Three overlapping genomic hSA clones were used to generate the hSA gene in transgenic mice. The three clones were λHAL-HA1, λHAL-H14 and λHAL-3W, as reported by Urano, et al. (1984), *Gene,* 32, 255–261 and Urano, et al. (1986), *J. Biol. Chem.,* 261 3244–3251. Briefly, a genomic library was constructed from a partial EcoRI digest of human fibroblast DNA. For the clone λHAL-3W, this library was screened with $^{32}$P-labeled human albumin genomic clones by hybridization in 1M NaCl, 50 mM Tris-HCl (pH 8.0), 10 mM EDTA, 0.1% SDS, 100 ug/ml of sheared salmon sperm DNA and 10× Denhardt's solution at 65° C. overnight after prehybridization in 3× SSC and 10× Denhardt's solution. Following hybridization, filters were washed in 0.2× SSC and 0.1% SDS at 65° C. The isolation of the λHAL-HA1 clone was identical except that a 0.9 kb BglII-EcoRI fragment from the 5' end of λHAL-3W was used to screen the human fibroblast library. The clone λHAL-H14 was isolated from a library constructed with partial HindIII digested human liver DNA.

Figure 5:
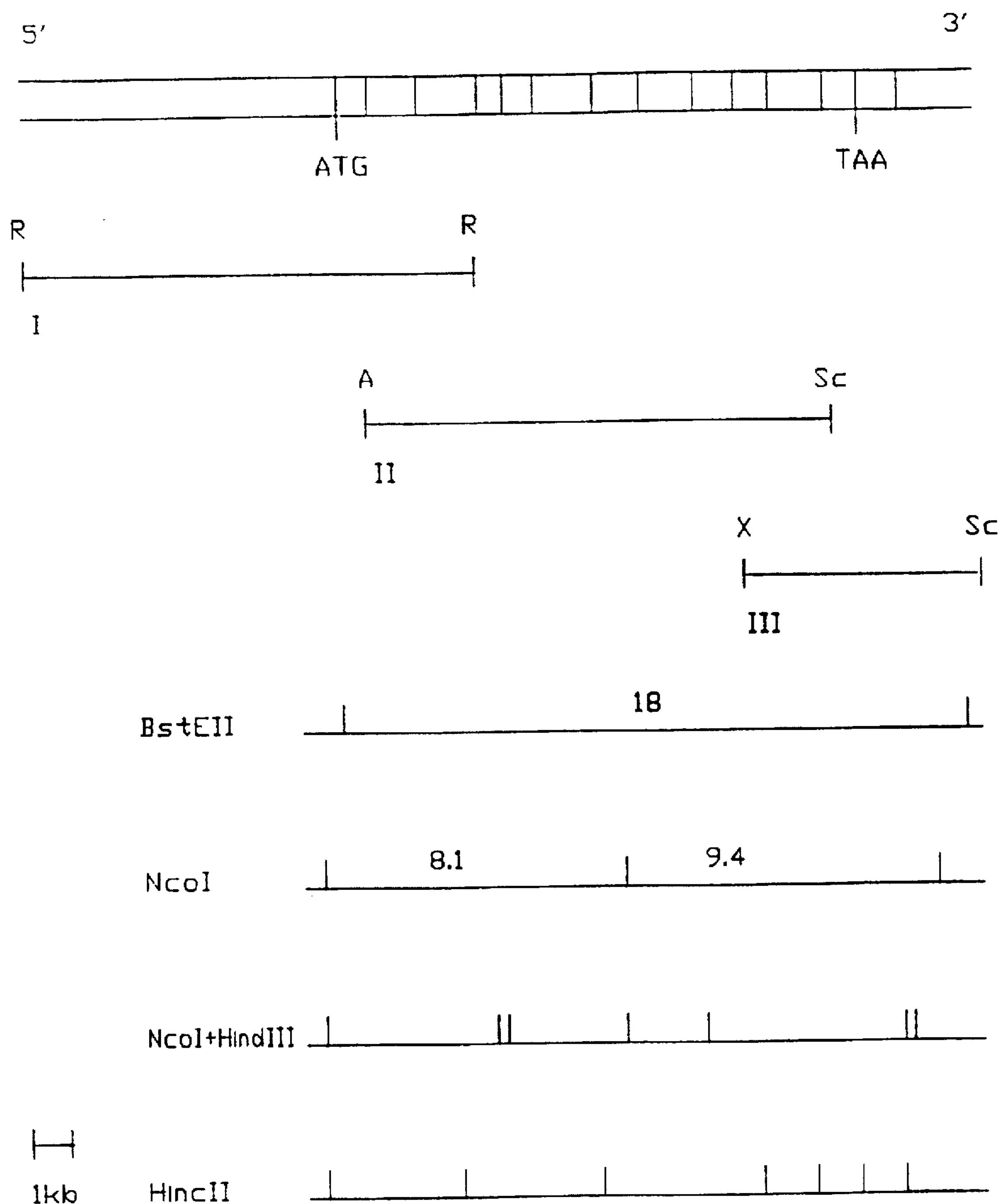
FIG. 5 depicts the DNA fragments used to construct the human serum albumin gone in transgenic mice.

These three hSA phage clones were used to generate three overlapping linear DNA fragments, which in composite comprised the whole hSA gene and flanking regions (See FIG. 5). The 5' most fragment I was 17 Kb partial EcoRI ("R" in FIG. 5) fragment isolated from λHAL-HA1, containing 13 kb of 5' flanking sequences and 3904 bp downstream of the transcription initiation site (+1). The middle fragment II was a 13.1 kb AcyI (=AhaII, and "A" in the figure) –SacI ("Sc") fragment of λHAL-3W and runs from +1405 to +14546 bp. The 3' most fragment III was a 6.7 kb XhoI ("X") –SalI fragment of λHAL-H14 (FIG. 5) and runs from +12694 to +19.4 kb and contains 2.5 bk of 3' flanking sequence. The overlapping regions are 2.5 kb (fragment I and II) and 1.85 kb (fragment II and III). Both regions contain exons and introns. Fragments I, II, and III span a 33 kb region comprising the 17.0 kb structural hSA gene. In FIG. 5, black boxes indicate exons, white regions represent introns and flanking sequences. Restriction sites used to generate unique fragments diagnostic of homologous recombination events are indicated in the lower part of the figure. Also in the figure, ATG refers to the translation initiation codon for hSA and TAA refers to the translation termination codon.

All three fragments were subcloned. Prior to microinjection, plasmid sequences were completely removed using the indicated restriction enzymes. The fragments were purified from low melting point agarose. In most cases (see Table I), the fragments were treated with klenow DNA polymerase and dNTP's to fill in overhanging sticky ends. The resultant blunt ended fragments were then treated with bacterial alkaline phosphatase to remove the 5' phosphate groups. The overlapping DNA fragments were next concentrated then coinjected into the male pronuclei of fertilized mouse eggs according to published methods (Hogan, et al. (1986) in "Manipulating the Mouse Embryo: A Laboratory Manual", Cold Spring Harbor Laboratory). While the number of molecules injected varied from ≈25 to ≈100 per egg cell, the ratio of the individual fragments was approximately 1:1:1. Embryos were implanted into the uteri of pseudo pregnant female mice according to the methods of Hogan, et al., supra.

To assay correct homologous recombination of the three overlapping fragments and integration of the nascent transgene into the mouse genome, genomic DNA from the newborn pups was subject to the following specific digestions followed by Southern hybridization with hSA cDNA probes:

Bst EII: cuts outside the hSA gene region and yields an 18 kb band if correct recombination occurred (See FIG. 5);

Nco I: cuts outside the overlapping regions and yields bands of 8.1 and 9.4 if correct recombination occurred;

Nco I+Hind III: cuts at several positions outside the region of overlap, indicative of the presence of intact fragments;

Hinc II: cuts in the overlapping regions, yielding several bands indicative of correct arrangement in these regions.

Figure 6:
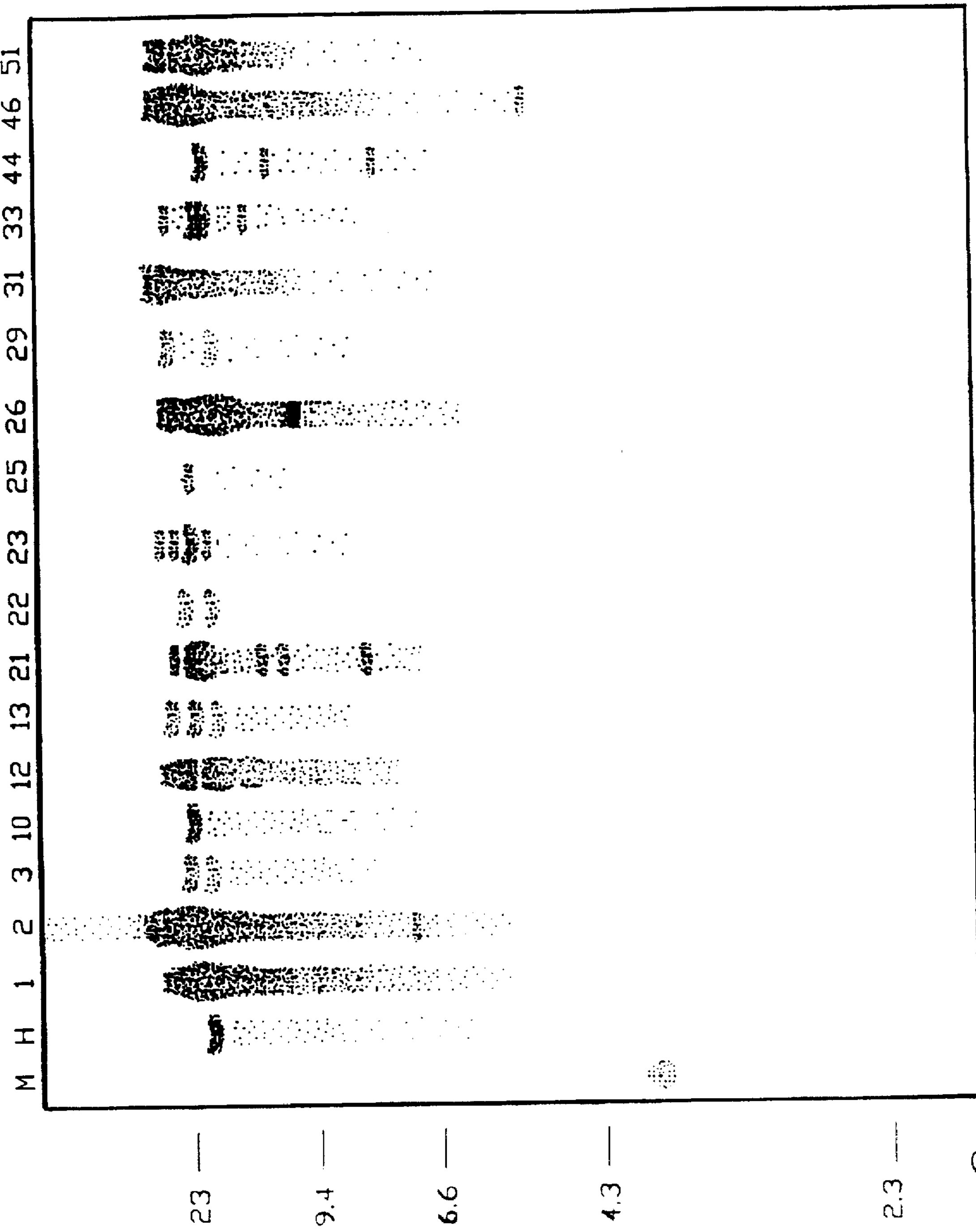
FIGS. 6 and 7 are Southern Blots of chromosomal DNA from the transgenic mice of Example 1.
Figure 7:
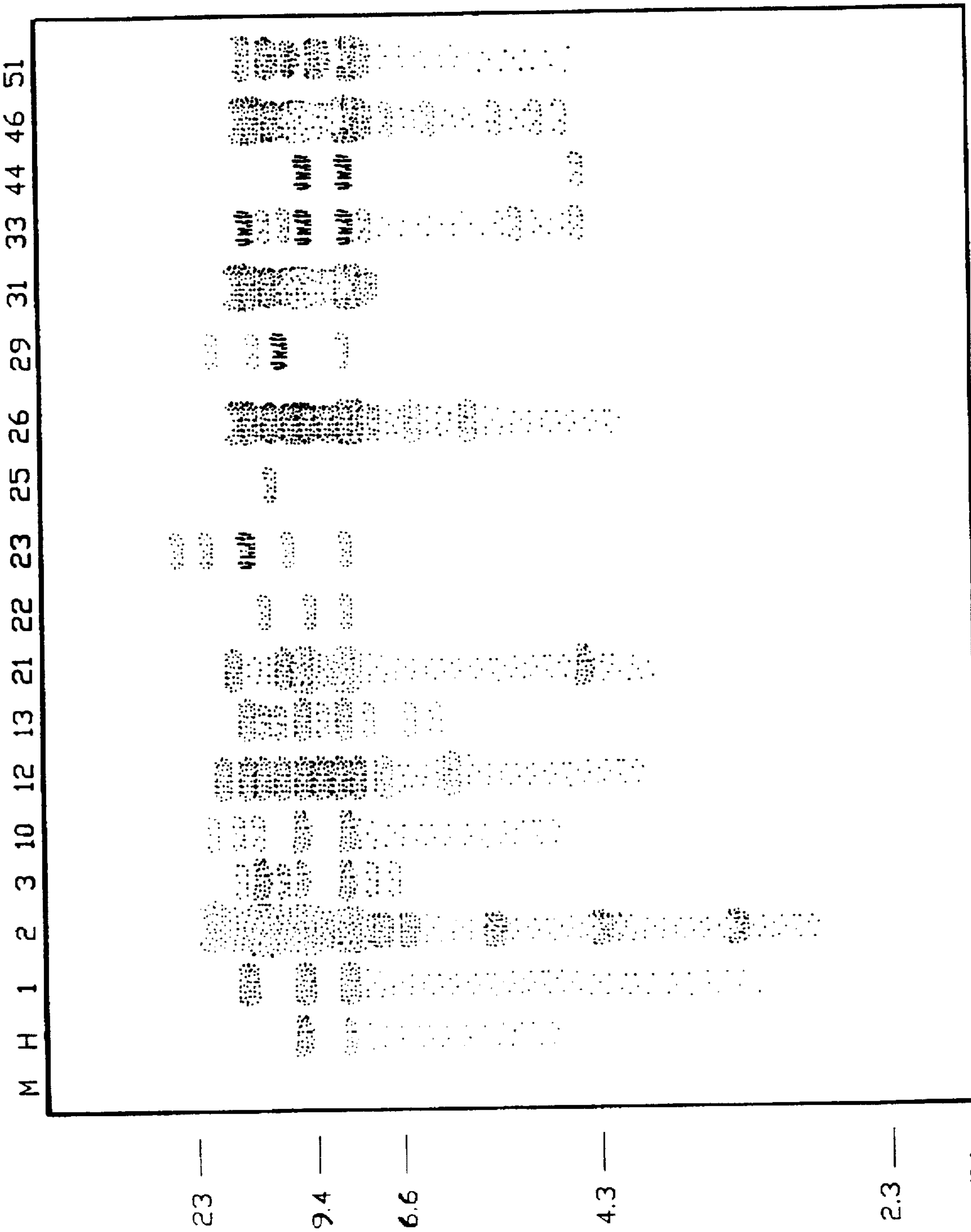

Chromosomal DNA was isolated either from various parts (including liver) of 3 day old mice, or from tails of adult mice. Transgenic animals were identified by Southern Blotting using a full length hSA cDNA probe. Results for 17 mice are shown in FIGS. 6 and 7. DNA (10 ug) from these mice was digested with NcoI (FIG. 6); BstEII (FIG. 7); NcoI+HindIII (double digest; data not shown); and HincII (data not shown); run on a 0.6% agarose gel, transferred to Highbond-N (Amersham) and hybridized to a full length hSA cDNA probe. Hybridizing bands of 9.4 and 8.1 (NcoI digest) or 18 kb (BstEII digest) are presnt only when the coinjected DNA fragments contain the overlapping regions from fragments I and II, and from II and III, respectively. The 18 kb BstEII fragment spans both overlapping regions and contains the complete 17 kb structural hSA gene. A total of 20 transgenic mice appeared to contain the intact hSA gene locus as judged by the presence of all the diagnostic bands. Of the remaining 7 mice, 6 had incorporated DNA resulting from recombination between fragments I and II (lanes numbered 23, 25, 29, 31, and 46 in FIGS. 6 and 7), one contained the recombinant product of II and III (not shown). At least 4 mice with the intact locus (22, 53, 63, and 67) were mosaic as judged by the absence of hSA DNA from some tissues or by copy number of less than one (data not shown).

In summary, these Southern Blots revealed that in initial experiments, of 107 mice born, 27 were found transgenic and 20 of these 27 transgenic animals correctly recombined and integrated all three fragments. These data are summarized in Table I below.

TABLE I

Numbers of transgenic mice expressing hSA

| fragments: | treated* | untreated | total |
|---|---|---|---|
| Transgenic mice | 23/73 | 4/34 | 27/107 |
| Transgenic mice with intact hSA locus | 16/23 | 4/4 | 20/27 |
| Mice expressing hSA | 9/14** | 4/4 | 13/18 |

*: Prior to micro injection, hSA DNA fragments were subjected to treatment with Klenow polymerase and bacterial alkaline phosphatase to generate dephosphorylated blunt ends.
**: At least 3 out of 5 nonexpressing mice were mosaic for the intact hSA gene. Nonexpressing mice for which analysis is shown in FIG. 2 are numbers 22 (mosaic), 26, and 33.

As can be seen in FIGS. 6 and 7, homologous recombination between all three overlapping DNA fragments provided the predominant integrant and was detected in 74% of the transgenic mice. Moreover, all transgenic mice contained hSA fragments resulting from homologous recombination between at least two overlapping fragments.

Ten of the 20 mice containing the complete hSA transgene were analyzed for expression of the gene at the level of transcription. Polymerase chain reactions (PCR) were performed following a reverse transcriptase (RT) reaction performed on 1 ug of total liver DNA as previously described (Kawasaki, E. S. in PCR Protocols (eds. Innis, M. et al.); 21–27 (Acad. Press, Inc., San Diego, 1990). A region from the resulting cDNA was amplified by PCR using primers complementary to part of hSA exons 12 and 14. The PCR primers were selected for their low homology to mSA sequences and such that the amplified region included most of the transcribed sequences in the overlap between genomic fragments II and III. Digestion with SacI yields bands of 181 and 149 bp, digestion with DdeI results in bands of 192 and 138 bp. RT-PCR on control mouse liver RNA never resulted in amplification (not shown). Similarly, RT-PCR on 6 mice which contained recombined hSA fragments but not the intact hSA locus resulted in no amplification. PCR was performed for 35 cycles of denaturation (1 minute at 92° C.), annealing (1 minute at 41° C.) and extending (2 minutes at 72° C.) essentially as described in Kawasaki et. al (supra). The $MgCl_2$ concentration was 2.5 mM. Sequence of forward primer (from 13853 to 13878 in exon 12):

5'-CAGATCACCAAATGCTAGCACAGA-3';

Reverse primer (from 15964 to 15991 in exon 14):

5'-AGCTTAGACTTAGCAGCAACAAGTTTTTT-3'.

Figure 8:
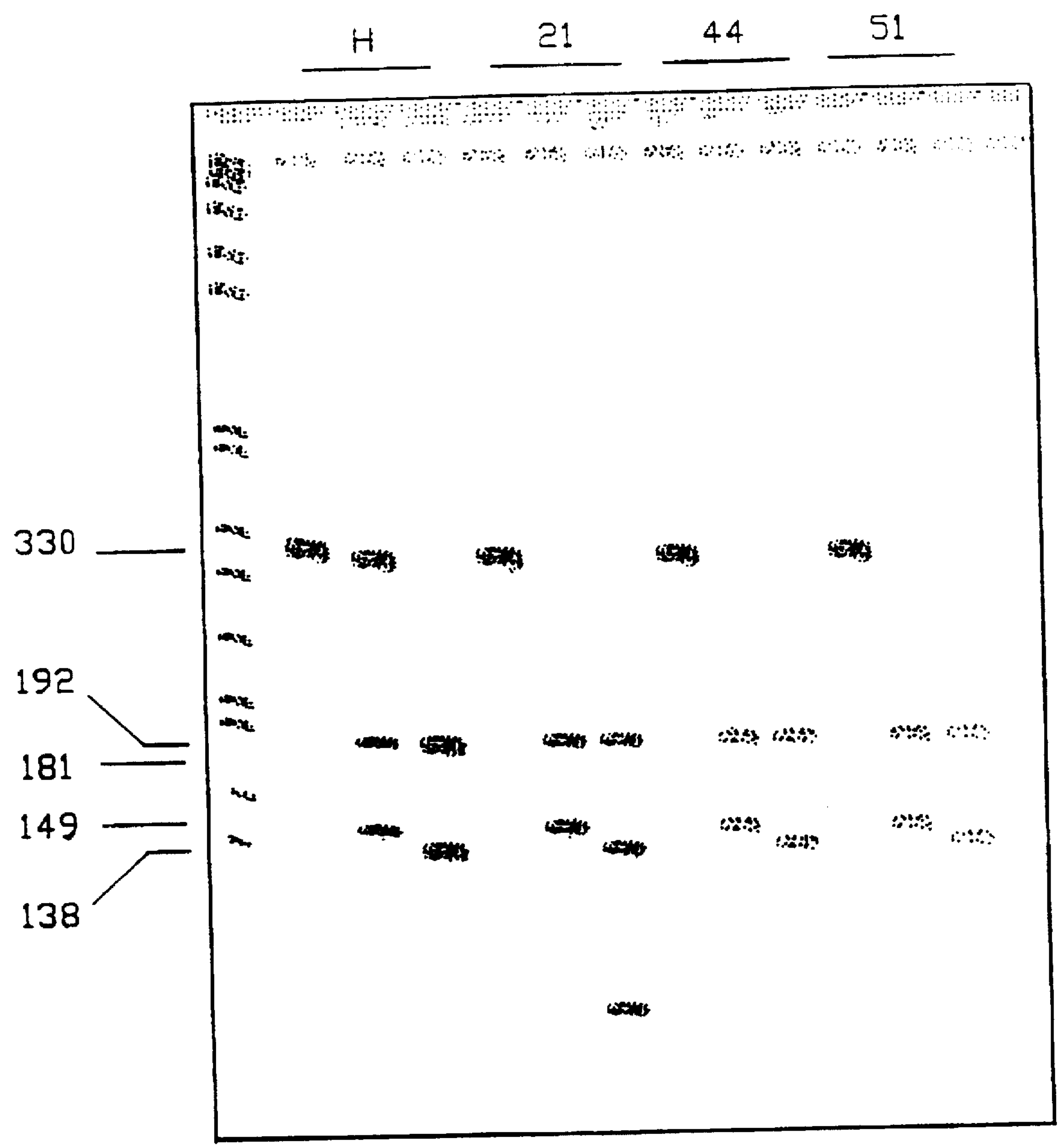
FIG. 8 is an ethidium bromide-stained agarose gel, containing amplified DNA (digested and undigested).

In FIG. 8, lane H is DNA amplified from human liver RNA; lanes 21, 44 and 51 are DNA amplified from liver RNA of hSA transgenic mice; lane S is amplified DNA digested with SacI; lane D is amplified DNA cut with DdeI; and the size marker is a 1 kbBRL ladder. Samples were separated on a 6% polyacrylamide gel.

Figure 9:
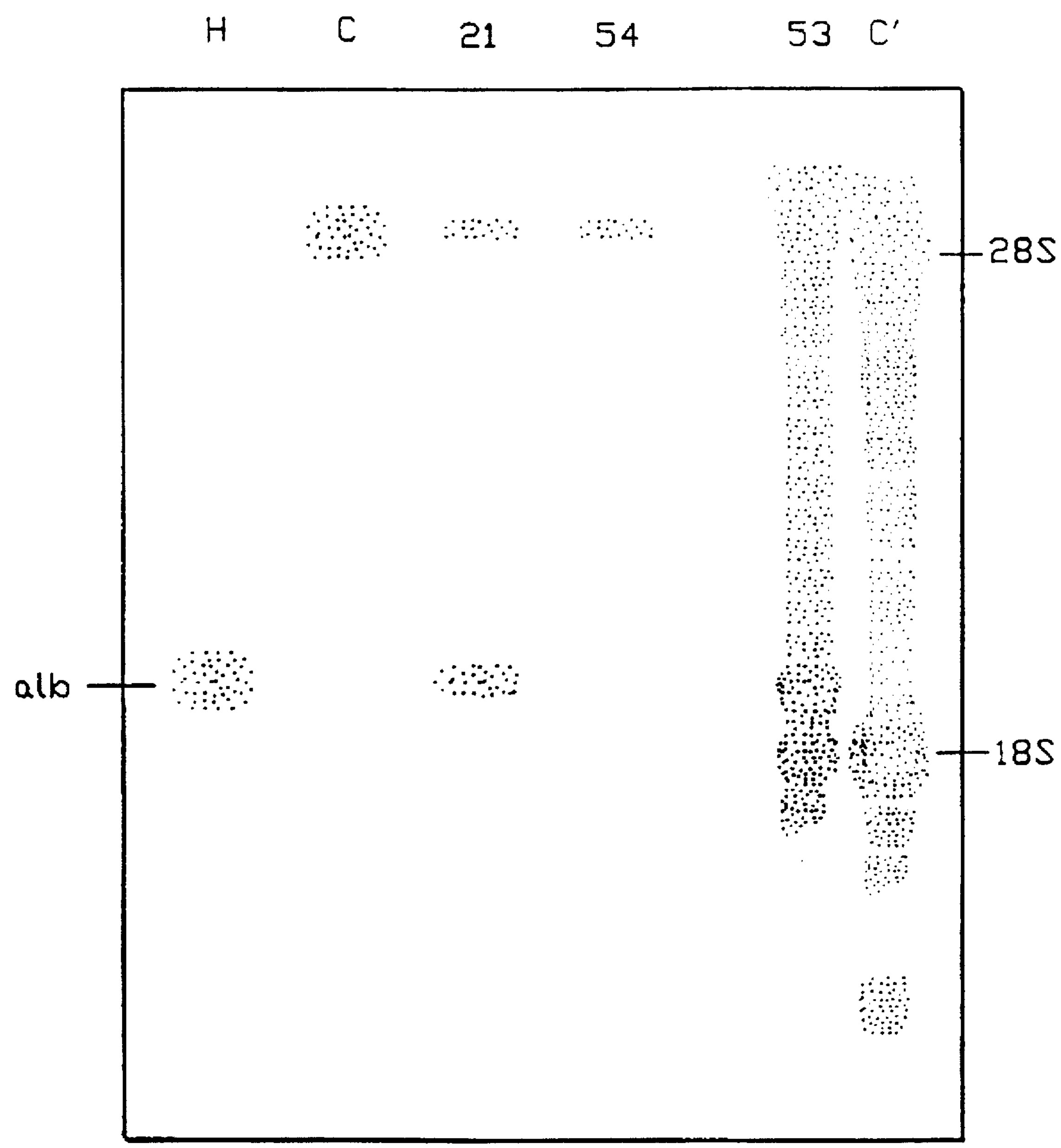
FIG. 9 is a Northern Blot of liver RNA from the hSA transgenic mice of Example 1.

In FIG. 9, lane H is total human liver RNA (1 ug); lane C is control mouse poly A+ selected liver RNA 20 (ug); lane 21 is a RNA of a mouse transgenic for the intact hSA gene (10 ug poly A+ RNA); lane 54 is RNA from a mouse transgenic for recombined hSA DNA fragments I and II (10 ug poly A+ RNA); lane 53 is RNA of a mouse transgenic for the hSA gene (20 ug total RNA); and C is RNA of a control mouse (20 ug total RNA). The results are representative for all mice—mouse 21 and 53 displayed relatively high expression levels. Total and polyA+ RNA fractions were isolated from mouse livers as described in Maniatis et al., in Molecular Cloning: A Laboratory Manual (Cold Spring Harbor, N.Y.; Cold Spring Harbor Press, 1982); run on a 1% formamide gel; transferred to Highbond-N and hybridized to an end-labeled hSA specific synthetic primer complementary to hSA exon 14 (also used in RT-PCR, see above). In FIG. 9, "Alb" indicates position of hSA mRNA. 18 S and 28 S ribosomal RNA bands are visible due to aspecific hybridization of the labelled primer.

In summary, these experiments revealed that a band of the correct size was amplified from RNA samples of 7 of the 10 mice transgenic for the intact hSA gene. Restriction analysis using two different enzymes confirmed the identity of the amplified band as hSA. Analysis of total and polyA+ selected liver RNA from each transgenic mouse by Northern blotting using a hSA specific probe confirmed these findings and demonstrated that the hSA transcripts were of the correct size. Aberrant transcripts were never observed. Human serum albumin transcripts in these 10 mice were detected at levels $10^4$ to $10^5$-fold lower than in human liver.

A quantitative radioimmunoassay (RIA) for specific detection of hSA (i.e. the protein) in mouse serum was performed. A suspension of monoclonal anti-hSA antibodies (CL 2513A; Cedarlane Laboratories; Ontario, Canada) coupled to Sepharose (Pharmacia) was incubated with normal mouse serum (NMS) to which hSA had been added to 10 ug/ml (black dots in FIG. 10); with transgenic mouse serum (representative curve of mouse 53 serum; open circles); or with NMS only (large black dot). RIA procedures were essentially as described in Nuijens, J. H., et. al, (1989), J. Biol. Chem. 264, 12941–12949. Sepharose-bound hSA was quantified by incubation with affinity purified anti-hSA polyclonal rabbit antibodies (Sigma Chemical Co.) labeled with $^{125}$I. Prior to radioiodination, these purified antibodies were incubated with NMS-Sepharose to remove mouse serum albumin cross-reactive antibodies. Subsequently, Sepharose-bound radioactivity was measured. Results are expressed in FIG. 10 as percentage of the labeled antibodies added. The amount of serum is indicated (abscissa). The level of hSA in the sera of transgenic mice were calculated from the paralel dose-response curves. The lower limit of detection of this RIA was ca. 5 ng. HSA was only detected in serum from mice containing the intact hSA.

Figure 11:
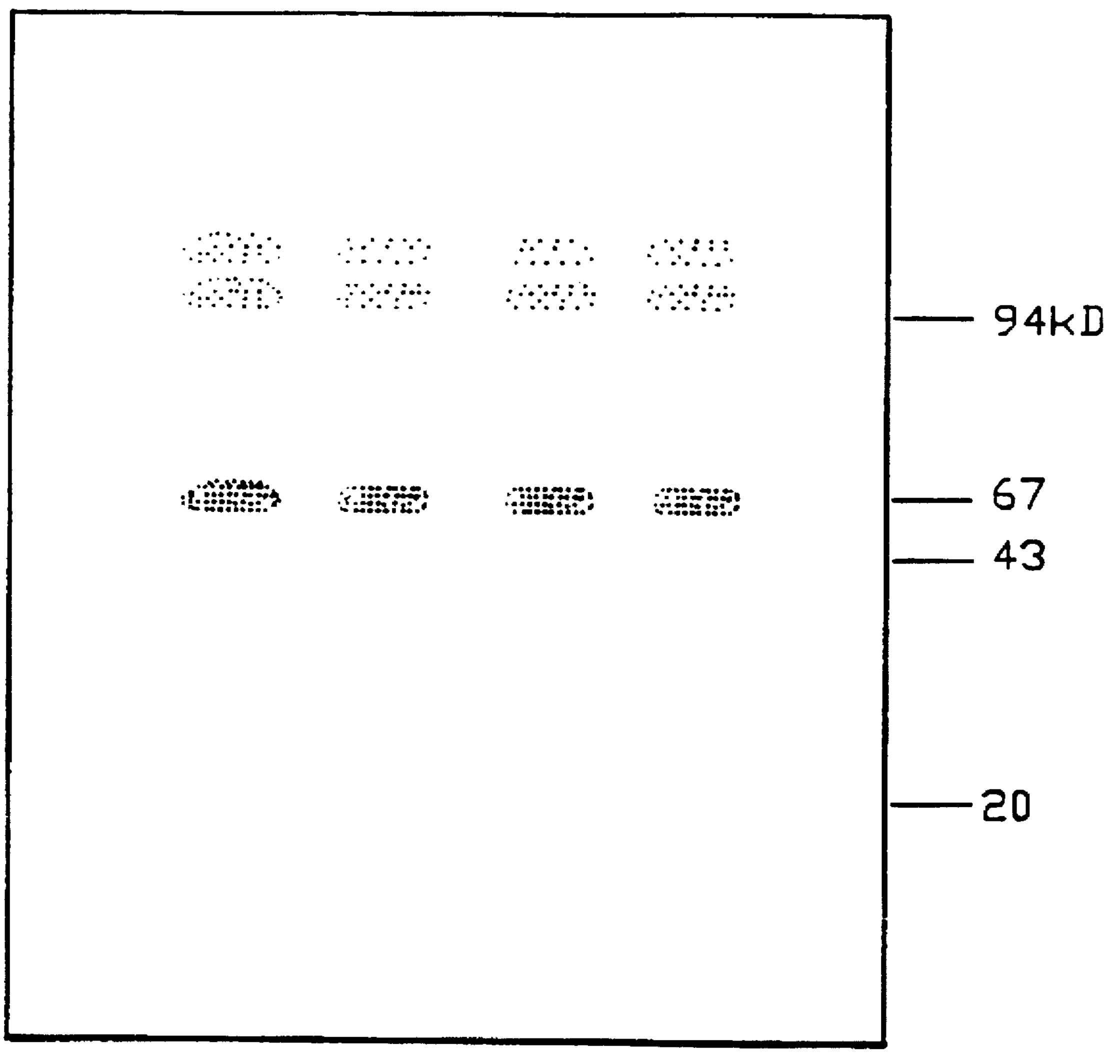
FIG. 11 is a Western Blot characterizing the hSA produced by hSA transgenic mice of Example 1.

For the Western blots, procedures were essentially as described in Nuijens, J. H., et. al, (1990), J. Clin. Invest. 84, 443–450. HSA was immunoprecipitated from 100 ul samples with Sepharose-bound monoclonal anti-hSA antibodies and dissociated into 10 ul of non-reducing SDS-sample buffer. One ul samples were analyzed by SDS-PAGE (10–15% w/v) followed by immunoblotting with polyclonal $^{125}$I-anti hSA antibodies. In FIG. 11, lane 1 is normal mouse serum, lane 2 is mouse 53 serum (containing 2.5 ug/ml·hSA), lane 3 is normal mouse serum to which 250 ng of purified hSA had been added, lane 4 is 250 ng purified hSA, lane 6 is 250 ng purified mSA, and lane 5 is a control of 25 ng of purified hSA directly subjected to SDS-PAGE.

Figure 10:
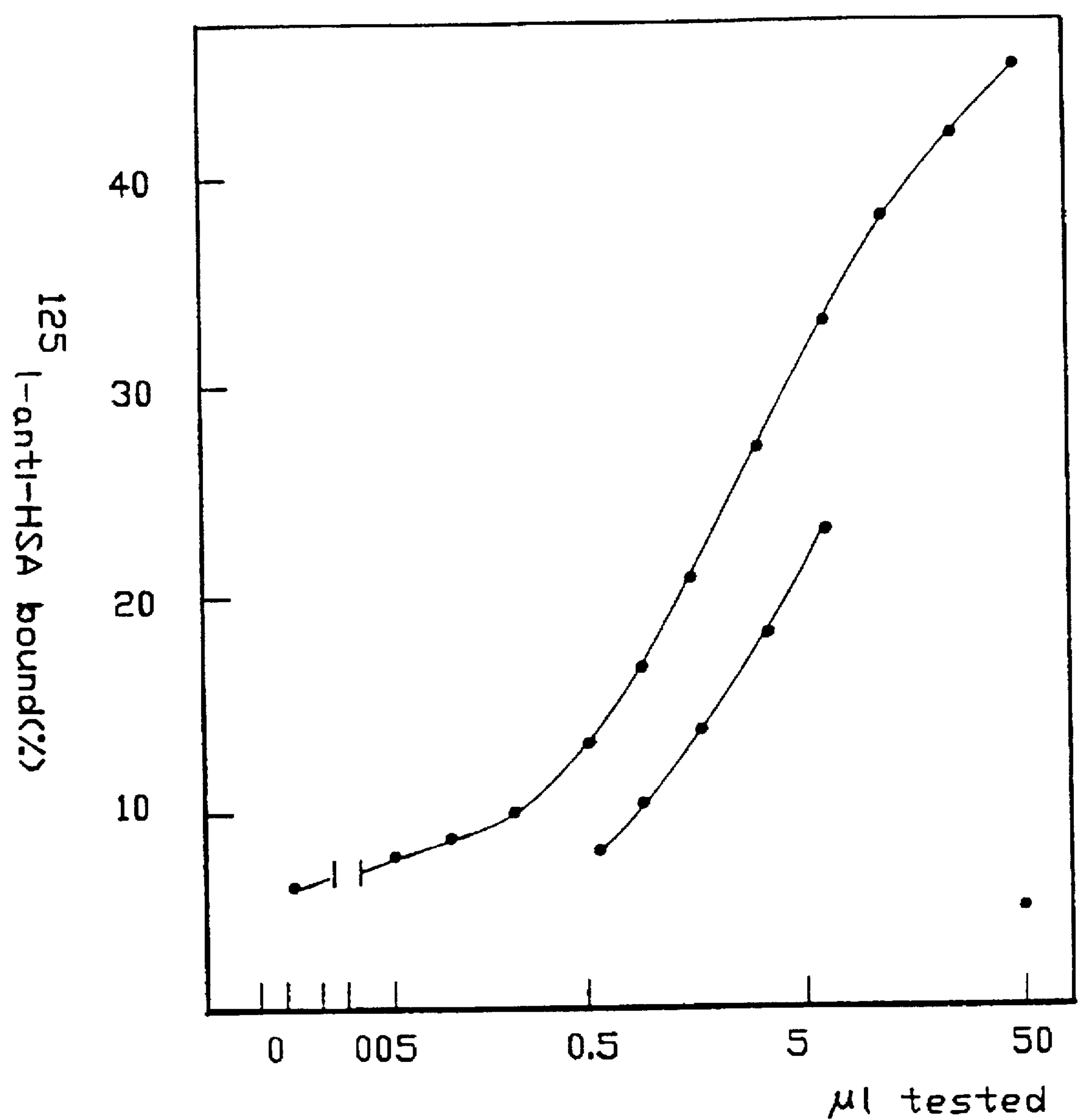
FIG. 10 is an RIA plot characterizing the hSA produced by hSA transgenic mice of Example 1.

Summarizing the results of these studies, of the 18 mice transgenic for the complete hSA gene, 13 expressed hSA and these 13 hSA positive mice included all 10 of the mice found to express hSA RNA by RT-PCR (above). The Western Blot data (FIG. 11) confirmed correct translation of the hSA gene by the hSA transgenic mice as initially established by RIA (FIG. 10).

EXAMPLE 2

Genomic Light Chain Human Ig Transgene Formed by In Vivo Homologous Recombination: Microinjection of Two Overlapping Fragments The following is exemplary of the in vivo generation of an immunoglobulin transgene from overlapping DNA fragments.

A map of the human K light chain has been described in Lorenz, W., et al. (1987), *Nucl. Acids Res.*, 15, 9667–9677.

A 450 kb XhoI to NotI fragment that includes all of Cκ, the 3' enhancer, all J segments, and at least five different V segments is isolated.

Briefly, nuclei are isolated from fresh human placental tissue as described by Marzluff, W. F., et al. (1985), "Transcription and Translaticn: A Practical Approach", B. D. Hammes and S. J. Higgins, eds., pp. 89–129, IRL Press, Oxford). The isolated nuclei (or PBS washed human spermatocytes) are embedded in a low melting point agarose matrix and lysed with EDTA and proteinase K to expose high molecular weight DNA, which is then digested in the agarose with the restriction enzyme NotI and XhoI as described by M. Finney in Current Protocols in Molecular Biology (F. Ausubel, et al., eds. John Wiley & Sons, Supp. 4, 1988, Section 2.5.1) The thus digested DNA is then fractionated by pulsed field gel electrophoresis as described by Anand, R., et al. (1989), *Nucl. Acids Res.*, 17, 3425–3433. Fractions enriched for the NotI/XhoI fragment are assayed by Southern hybridization to detect one or more of the sequences encoded by this fragment. Those fractions containing this NotI/XhoI fragment are pooled and cloned into the vector pYACNN in yeast cells. pYACNN is prepared by digestion of pYAC-4 Neo (Cook, H., et al. (1988), *Nucleic Acids Res.*, 16, 11817) with EcoRI and ligation in the presence of the oligonucleotide 5'-AAT TGC GGC CGC-3'.

YAC clones containing the heavy chain NotI/XhoI fragment are isolated as described by Brownstein, et al. (1989), *Science*, 244, 1348–1351, and Green, E., et al. (1990), *Proc. Natl. Acad. Sci. USA*, 87, 1213–1217. The cloned insert is isolated from high molecular weight yeast DNA by pulse field gel electrophoresis as described by M. Finney, opcit.

A 750 kb MluI to NotI fragment that includes all of the above plus at least 20 more V segments is similarly isolated and digested with BssHII to produce a fragment of about 400 kb.

The 450 kb XhoI to NotI fragment plus the approximately 400 kb MluI to BssHII fragment have sequence overlap defined by the BssHII and XhoI restriction sites. The DNA fragments are condensed by the addition of 1 mM spermine and microinjected directly into the nucleus of single cell embryos previously described so that multiple copies of each fragment are present in each injected zygote. Homologous recombination of these two fragments upon microinjection of a mouse zygote results in a transgene containing at least an additional 15–20 V segments over that found in the 450 kb XhoI/NotI fragment.

EXAMPLE 3

Human Lactoferrin Transgene Formed by In Vivo Homologous Recombination: Microinjection of Two Overlapping DNA Fragments To obtain the entire hLF genomic clone, two human genomic cosmid libraries were screened using an hLF cDNA clone (described in PCT Publication No. PCT/US90/06874 published June 1991) as a probe. Of 14 clones isolated, 2 clones (designated 13.1 and 13.2; one from each human cosmid library) contained the entire hLF gene as determined by hybridization with primers specific for the first and last (17th) hLF exons and by DNA sequencing. These cosmid clones range from 35–40 kbp in size. Clone 13.1 contains approximately 4 kbp additional 3' flanking sequence; clone 13.2 contains additional 5' flanking sequence.

The most 5' ApaI site is located in exon I, in the hLF signal sequence. The 400 bp region immediately 5' of exon I was sequenced. This region contains the transcription initiation site of the hLF gene and a TATA-box. This region also includes a BamHI restriction site.

To construct a mammary gland specific expression vector it was necessary to fuse the 16 kbp αs1 bovine casein promoter region to the genomic hLF clone. However, the total size of such a construct, about 60 kb (16 kb (promoter) +8 kb (cosmid vector)+35–40 kb (hLF genomic clone)= 59–64 kb), renders the use of conventional cloning vectors difficult. Therefore, the 16 kbp αs1 casein promoter was fused to the 5' 9 kb region of the structural hLF gene and this fragment was coinjected with and overlapping hLF fragment containing the most 3' 30 kbp of clone 13.1.

The BamHI fragment (containing exon I) from clone 13.2 was subcloned into the plasmid pUC19. From this clone, a 8.9 kbp ApaI-SalI fragment was isolated by ApaI (partial digest) and SalI digestion. This fragment lacks most of the hLF signal sequence and all of the hLF 5' UTR. A sequence representing this missing region was obtained by synthesizing 2 complementary DNA strands (a 68- and a 62-mer) which runs from the 5' ApaI site into the downstream region from the hLF TATA-box. After annealing these primers a DNA fragment is generated which has a 5' ClaI overhang and a 3' ApaI overhang. This synthetic ClaI-ApaI fragment and the 8.9 kbp ApaI-SalI fragment described above were ligated into p-16kbCS and into a similar plasmid, containing 8 kbp instead of 16 kbp of the as1 casein promoter. This yields two plasmids, containing 16 kbp or 8 kbp of bovine as1 casein promoter, fused to the 5' part (9 kbp) of the hLF genomic gene. These fragments were cut out (NotI-SalI) and coinjected with the 3' 30 kbp ClaI fragment from hLF cosmid clone 13.1. The coinjected fragments had an overlap of 2.7 kbp.

Microinjections of zygotes and generation of transgenic animals is performed as described in Example 1 for transgenic mice and as described in PCT Publication No. PCT/US90/06874 for transgenic bovine species.

EXAMPLE 4

Genomic Light Chain Human Ig Transgene Formed by In Vivo Homologous Recombination: Microinjection of a Single Large DNA Segment The following is another example of the in vivo generation of an immunoglobulin transgene from overlapping DNA fragments.

This example is identical to Example 2 except that multiple copies of the 750 kb MluI to NotI DNA molecule are microinjected directly into the nucleus of mouse zygotes without prior condensation with spermine.

An analysis of the DNA from transgenic offspring confirm the presence of the full length 750 kb DNA transgene integrated into the genome of the animal.

Having described the preferred embodiments of the present invention, it will appear to those ordinarily skilled in the art that various modifications may be made to the disclosed embodiments, and that such modifications are intended to be within the scope of the present invention.

What is claimed is:

1. A method for generating a DNA segment inside a cell comprising the step of introducing at least a first and a second DNA fragment into a recombination competent mammalian cell, each of said DNA fragments having a 5' and a 3' sequence portion, said first DNA fragment 3' sequence portion having at least 80% sequence identity to said second DNA fragment 5' sequence portion, wherein said first and second DNA fragment homologously recombine in said cell to form are combined DNA segment greater than 50 kb in length, said recombined DNA segment being integrated into the genome of said cell.

2. The method of claim 1, wherein said cell is selected from the group consisting of endothelial cells, epithelial cells, myoblasts, hepatocytes, leukocytes, hematopoetic stem cells, fibroblasts, ES cells, and non-human zygotes.

3. The method of claim 1, wherein said cell is a non-human zygote.

4. The method of claim 1, wherein said co-introducing step is performed by microinjection.

5. The method of claim 1, wherein said recombined DNA segment encodes a protein.

6. The method of claim 5, wherein said protein is a human immunoglobulin.

7. The method of claim 5, wherein said protein is human lactoferrin.

8. A method for generating a DNA segment inside a cell comprising the step of introducing at least a first and a second DNA fragment into a recombination competent mammalian cell, each of said DNA fragments having a 5' and a 3' sequence portion, said first DNA fragment 3' sequence portion having at least 80% sequence identity to said second DNA fragment 5' sequence portion, wherein said first and second DNA fragment homologously recombine in said cell to form a recombined DNA segment of at least 50 kb integrated into the genome of said cell, and said DNA segment does not encode a positive selection marker which can be used to detect homologous recombination between said first and said second fragments.

9. A method for generating a DNA segment inside an embryonic cell comprising the step of introducing at least a first and a second DNA fragment into a mammalian embryonic cell, each of said DNA fragments having a 5' and a 3' sequence portion, said first DNA fragment 3' sequence portion having at least 80% sequence identity to said second DNA fragment 5' sequence portion, wherein said first and second DNA fragment homologously recombine in said embryonic cell to form a recombined DNA segment of at least 50 kb, said recombined DNA segment being integrated into the genome of said embryonic cell.

10. The method of claim 2, wherein said embryonic cell is a zygote.

11. A transgenic mammalian cell comprising a transgene longer than about 50 kb integrated into the genome of the cell wherein the transgene expresses a protein at a detectable level, and the mammalian cell is a non-human zygote or a non-human mammalian embryonic stem cell capable of populating the germline of a mammal.

12. A transgenic non-human mammal containing a transgene integrated into the genome of the mammal, comprising a recombined DNA segment of at least 50 kb formed by homologous recombination of a first and a second DNA fragment, each of said DNA fragments having a 5' and a 3' sequence portion, said first DNA fragment 3' sequence portion having at least 80% sequence identity to said second DNA fragment 5' sequence portion, wherein the transgene expresses a protein at a detectable level.

13. The mammal of claim 12, wherein said protein is a human immunoglobulin.

14. The mammal of claim 12, wherein said protein is human lactoferrin.

15. The mammal of claim 12, wherein said mammal is selected from the group of murine species.

16. The mammal of claim 12, wherein said mammal is selected from the group of bovine species.

17. A transgenic nonhuman mammal comprising a transgene longer than 50 kb integrated into the genome of the mammal, wherein the transgene expresses a protein at a detectable level.

18. The transgenic nonhuman mammal of claim 12, wherein the transgene is smaller than 500 kb.

19. The transgenic nonhuman mammal of claim 15, wherein the transgene includes a positive selection marker.

20. The cell of claim 11, wherein the transgene comprises greater than 50 kb of DNA heterologous to the cell.

21. The cell of claim 11, wherein the transgene comprises greater than 50 kb of DNA homologous to the cell and integrated into the cell genome other than at its natural position.

22. The transgenic nonhuman mammal of claim 17, wherein the transgene comprises greater than 50 kb of DNA heterologous to the cell.

23. The transgenic nonhuman mammal of claim 17, wherein the transgene comprises greater than 50 kb of DNA homologous to the cell and integrated into the cell genome other than at its natural position.

* * * * *